United States Patent

Konik et al.

[11] Patent Number: 5,959,009
[45] Date of Patent: Sep. 28, 1999

[54] MASCARA WATERPROOFING COMPOSITION

[75] Inventors: Richard A. Konik, Sayville; Rachel J. Painter, E. Setauket; George J. Stepniewski, Melville, all of N.Y.

[73] Assignee: E-L Management Corp, New York, N.Y.

[21] Appl. No.: 08/962,100

[22] Filed: Oct. 31, 1997

[51] Int. Cl.$^6$ ...................................................... C08K 5/24
[52] U.S. Cl. .......................... 524/261; 524/275; 524/277; 524/487; 524/488; 524/489; 524/490; 525/93; 525/95; 525/96; 525/191; 525/203; 525/205
[58] Field of Search ..................................... 524/261, 275, 524/277, 487, 488, 489, 490; 525/93, 95, 96, 191, 203, 205

[56] References Cited

U.S. PATENT DOCUMENTS 5,389,363  2/1995  Snyder et al. ........................... 424/70.7
5,756,082  5/1998  Cashin et al. ......................... 424/78.03

FOREIGN PATENT DOCUMENTS

| 497144 B1 | 5/1992 | European Pat. Off. . |
| WO 92/19215 | 11/1992 | WIPO . |
| WO 94/12190 | 6/1994 | WIPO . |
| WO 94/17775 | 8/1994 | WIPO . |
| WO 97/29842 | 8/1997 | WIPO . |
| WO 98/42298 | 10/1998 | WIPO . |

*Primary Examiner*—Edward J. Cain
*Attorney, Agent, or Firm*—Dorene M. Price, Esq.; Karen A. Lowney, Esq.

[57] ABSTRACT

The invention relates to waterproof or water resistant compositions for application to the lashes comprising a styrene-ethylene-propylene copolymer as gellant, a film forming agent, and a volatile oil.

20 Claims, No Drawings

MASCARA WATERPROOFING COMPOSITION

FIELD OF THE INVENTION

The invention relates to a cosmetic composition for application to the eyelashes. More specifically, the invention relates to compositions for waterproofing mascara.

BACKGROUND OF THE INVENTION

There are many situations in which a mascara which is substantially impervious to water is desirable. Walking in the rain, swimming, jogging or any other strenuous physical exercise are all activities likely to test the limits of durability of the average mascara. Nonetheless, it is frequently difficult or impossible to change from one mascara to another when starting a new activity. This means that the wearer will have to commit herself to the permanent use of a waterproof mascara even under circumstances which may not call for it, simply because it might be needed at some time in the future. Many women find regular use of waterproof mascara unappealing, however, because it can often be very thick and heavy, and also can be very difficult to remove. Thus, the user is forced to choose between using the non-waterproof mascara she actually prefers but risking potential displacement of mascara from lashes to cheeks in an unexpected rainstorm, or regularly using a waterproof mascara which is not aesthetically pleasing to her, but which will reliably stay put on her lashes, regardless of her activity.

The present invention now provides a means by which a mascara wearer can choose when she wishes to waterproof her lashes, while still maintaining regular use of her favored non-waterproof mascara.

SUMMARY OF THE INVENTION

The present invention relates to a cosmetic composition for application to the lashes comprising a volatile oil solvent, a film-forming agent, and a styrene-ethylene-propylene copolymer as gellant. The composition is useful as a waterproofing agent for mascara, capable of being applied over mascara when needed. The composition also provides a base for a waterproof mascara product, which is obtained by adding pigment to the composition.

DETAILED DESCRIPTION OF THE INVENTION

Waterproofing compositions for the lashes have previously been described, for example, in WO 92/19215. The formulations disclosed therein are similar in their basic elements to the formulations of the present invention, but do not disclose a styrene-ethylene-propylene copolymer as gellant. The useful copolymers are known in the art, and they have been used in cosmetic compositions, as described in EP 497 144, but have not been disclosed in compositions for application to the lashes, nor in waterproofing compositions for the lashes. Surprisingly, a significant advantage can be obtained by the use of such copolymers as the principle gellant in a waterproofing composition. One of the more important aspects of any composition applied over mascara is that it be clear, so that the color of the mascara shines through. However, not all gellants routinely produce a clear product. For example, WO 92/19215 discloses a preferred clay-based gellant, bentone, which when used alone may not always produce a clear gel. Moreover, the use of clay-based gellants like bentone as the sole gellant, depending on the film-forming agent employed, can result in a product which is unstable, allowing leakage of solvents and emollients from the gel matrix. In contrast, the use of a styrene-ethylene-polypropylene copolymer as gellant results in a clear shiny product which does not cloud the mascara when applied over it; the product so prepared also retains stability over prolonged periods of time, thereby producing a superior product.

The copolymer gellants of the invention are particulate diblock copolymers having the formula S-EP, wherein "S" denotes a block comprising styrene monomers and "EP" denotes a block comprising ethylene and propylene monomers. These materials are well known in the art, and are available commercially, for example, from Shell Chemical Company, Oak Brook, Ill. under the tradename "Kraton® G rubber". A particularly preferred material is Kraton® G-1701X. The amount of the gellant used in the formulation is from about 1–15%, more preferably 5–10% by weight of the total composition.

The copolymer is combined with a volatile oil and a film-forming agent to prepare the waterproofing composition. The use of a volatile oil provides for a very quick-drying product, and confers maximum waterproofness. Suitable volatile oils for use in the composition include, but are not limited to both cyclic and linear silicones, such as hexamethylcyclotrisiloxane, octamethylcyclotetrasiloxane, and decamethylcyclopentasiloxane; or straight or branched chain hydrocarbons having from 8–20 carbon atoms, such as decane, dodecane, tridecane, tetradecane, and C8–20 isoparaffins. A preferred volatile oil is a $C_9$–$C_{12}$ aliphatic hydrocarbon, such as is commercially available under the tradename Permethyl® 99A, from Permethyl Corp., Frazer, Pa.). The volatile oil constitutes from about 1–90%, preferably about 50–85%, by weight of the total composition.

A second component is a film-forming agent. The use of a film-former improves the wear of the composition, and can confer transfer-resistance to the makeup product. The film-forming agent may be any which is cosmetically acceptable for use around the eye. Examples of useful film-forming agents include natural waxes, polymers such as polyethylene polymers, and copolymers of PVP, ethylene vinyl acetate, dimethicone gum, and resins, such as shellac, polyterpenes, and various silicone resins, e.g., trimethylsiloxysilicate. The film-former is used in an amount of from about 0.1–50%, more preferably from about 1–20%. A particularly preferred film-former is a PVP/eicosene copolymer, which produces a smooth, non-tacky film on the lashes. Such copolymers are commercially available under the tradename Ganex® from GAF.

In a preferred embodiment, the composition contains less than 5%, and preferably none, of a non-volatile oil component. The use of a non-volatile oil can cause plasticizing of the film-forming agent, thereby reducing the product's resistance to smudging. The absence of a non-volatile oil thus results in a product with greater wear. With the use of a pliable film-former such as Ganex®, a non-volatile oil is unnecessary to soften it; however, if a harder, or more brittle, film-former is used, a small amount of non-volatile oil may be necessary to achieve the desired consistency of the product.

The waterproofing compositions of the invention may also comprise additional, optional components. For example, it may be desirable to add one or more preservatives or antioxidants to the formulation. Appropriate preservatives may include propyl paraben, butyl paraben, mixtures thereof, or isoforms thereof, as well as BHA or BHT.

In an alternate embodiment of the present invention, the composition provides the base for a waterproof mascara. In this embodiment, the composition contains one or more colorants or pigments. Any pigment appropriate for use in the eye area may be used. Examples of useful pigments are metallic oxides, such as titanium or iron oxides, bismuth oxychloride, carmine, chromium oxide or chromium hydroxide greens, ultramarines, ferric ferrocyanide, ferric ammonium ferrocyanide, mica, FD&C blue No. 1, FD&C Red No. 40, FD&C yellow No. 5, and FD&C green No. 5. Pigment will typically be used in an amount of up to about 20%, preferably at about 1–10% by weight of the composition as a whole.

If the waterproof composition is to be used as a mascara, it may also be desirable to add additional components, particularly viscosifying agents such as waxes and other gellants, in an amount of from about 1–10%, preferably up to about 5%. The waxes may be any synthetic or natural waxes which are suitable for use in the eye area; preferably, the wax is plant-derived, for example, carnauba or candelilla wax. The gellant may be, for example, bentone, triglycerides, aluminum stearate, $C_{18}$–$C_{36}$ acid glycol esters, glyceryl tribehenate and the like. Other viscosifying agents include alginates, carbomers, celluloses, gums, carageenans, starches or silicates. Fillers can also optionally be added, in an amount of about 1–20%, preferably from about 1–10%; these may be, for example, silica, PMMA, nylon, alumina, barium sulfate or any other filler typically used in such compositions.

The lash compositions of the invention are easily used by the consumer. As a simple waterproofing agent, the product is applied to upper and/or lower lashes, over an existing coat of mascara, after the mascara has completely dried. If the composition is used as a waterproof mascara, it is simply applied directly to the lashes, or over a coating of lash primer.

The invention is further illustrated by the following non-limiting examples:

EXAMPLES

Example I

A formulation according to the invention is prepared as follows:

| Material | Weight % |
| --- | --- |
| Phase 1 | |
| Isododecane | 61.05 |
| Phase 2 | |
| styrene-ethylene-propylene copolymer | 12.00 |
| BHT | 0.05 |
| Phase 3 | |
| isododecane | 17.40 |
| PVP/eicosene copolymer | 9.00 |
| isododecane/quaternium-18 hectorite | .50 |

The Phase 2 components are dissolved in Phase 1 component at about 90° C., and mixed to homogeneity. Phase 3 components are then heated to 90° C., mixed to homogeneity, then added to the combined Phases 1 and 2, mixed thoroughly, then cooled to produce the final product.

Example 2

Stability of a composition substantially as described in Example 1, containing a styrene-ethylene-propylene copolymer as gellant, is compared with the same composition containing only bentone as the gellant. Specifically, the composition of the invention is prepared with about 7% copolymer, while two bentone compositions, without the copolymer, contain about 2.1% and about 5.2% bentone alone as gellant. The composition of the invention upon preparation is homogeneous and stable, and remains in this condition for an observation period of several weeks. On the other hand, the two bentone-containing compositions are immediately unstable, with the bentone separating out into a bottom phase, with a water-thin top phase.

Example 3

The waterproofing properties of the compositions of the invention are tested by application over non-waterproof mascaras. Artificial eyelashes are glued to a series of five glass slides, and to each is applied the same non-waterproof mascara; the mascara is allowed to dry, then a coat of a waterproofing composition is applied to all but one, which is left uncoated. A similar slide is prepared and a waterproof mascara is applied as a control. All slides are weighed, then agitated (100/min) in 50 ml of water. The slides are dried, and weighed again, to determine the weight of the material remaining on the lashes. Each sample is tested in duplicate. This number is then used to calculate the percent of mascara remaining on the lash after treatment.

The results show that, on average, about 92–94% of the mascara remained on the lashes after exposure to water. This compares favorably with the standard waterproof mascara, which retained about 95% mascara. In contrast, the uncoated lashes showed an average retention of about 29%.

What we claim is:

1. A waterproof or water resistant composition for application to the lashes comprising a styrene-ethylene-propylene copolymer as gellant, a film-forming agent selected from the group consisting of PVP copolymers dimethicone gum, shellac, polyterpenes, and silicone resins, and a volatile oil.

2. The composition of claim 1 in which the film-forming agent is a PVP/eicosene copolymer.

3. The composition of claim 1 in which the volatile oil is selected from the group consisting of cyclic and linear silicones, straight or branched chain hydrocarbons having from 8–20 carbon atoms, and C8–20 isoparaffins.

4. The composition of claim 1 in which the volatile oil is a $C_9$–$C_{12}$ aliphatic hydrocarbon.

5. The composition of claim 1 in which the styrene-ethylene-propylene copolymer is present in an amount of from about 1 to about 15%.

6. The composition of claim 1 in which the film-forming agent is present in an amount of from about 0.1 to about 50%.

7. The composition of claim 1 in which the volatile oil is present in an amount of from about 1 to about 90%.

8. The composition of claim 1 comprising a styrene-ethylene-propylene copolymer in an amount of from about 1 to about 15%, a PVP/eicosene copolymer in an amount of from about 0.1 to about 50%, and a volatile oil in an amount of from about 1 to about 90%.

9. The composition of claim 1 comprising a styrene-ethylene-propylene copolymer in an amount of from about 5 to about 10%, a PVP/eicosene copolymer in an amount of from about 1 to about 20%, and a volatile oil in an amount of from about 50 to about 85%.

10. The composition of claim 9 in which the volatile oil is a $C_9$–$C_{12}$ aliphatic hydrocarbon.

11. The composition of claim 10 in which the volatile oil is a $C_9$–$C_{12}$ aliphatic hydrocarbon.

12. The composition of claim 9 which comprises less than 5% of a non-volatile oil.

13. The composition of claim 10 which comprises less than 5% of a non-volatile oil.

14. The composition of claim 9 which comprises substantially no non-volatile oil.

15. The composition of claim 10 which comprises substantially no non-volatile oil.

16. The composition of claim 1 which also comprises a pigment.

17. The composition of claim 9 which also comprises a pigment.

18. The composition of claim 10 which also comprises a pigment.

19. A method of waterproofing mascara on the lashes which comprises applying over the mascara the composition of claim 1.

20. A method of waterproofing mascara on the lashes which comprises applying over the mascara the composition of claim 9.

* * * * *